(12) United States Patent
Miyagawa

(10) Patent No.: US 7,370,527 B2
(45) Date of Patent: May 13, 2008

(54) LIQUID LEVEL DETECTING APPARATUS

(75) Inventor: Isao Miyagawa, Kariya (JP)

(73) Assignee: Denso Corporation, Kariya, Aichi-pref. (JP)

( * ) Notice: Subject to any disclaimer, the term of this patent is extended or adjusted under 35 U.S.C. 154(b) by 331 days.

(21) Appl. No.: 11/322,347

(22) Filed: Jan. 3, 2006

(65) Prior Publication Data

US 2006/0144139 A1 Jul. 6, 2006

(30) Foreign Application Priority Data

Jan. 6, 2005 (JP) ............................. 2005-001910

(51) Int. Cl.
*G01F 23/00* (2006.01)
*G01F 23/28* (2006.01)

(52) U.S. Cl. .................. 73/290 V; 73/642; 73/644

(58) Field of Classification Search .............. 73/290 V, 73/642, 644, 290 R
See application file for complete search history.

(56) References Cited

U.S. PATENT DOCUMENTS

| 5,471,872 | A | * | 12/1995 | Cummings ................ 73/290 V |
| 7,117,738 | B2 | * | 10/2006 | Miyagawa et al. ....... 73/290 V |
| 7,204,142 | B2 | * | 4/2007 | Miyagawa et al. ....... 73/290 V |
| 2004/0020289 | A1 | | 2/2004 | Gouzou et al. |

FOREIGN PATENT DOCUMENTS

JP 06-249697 9/1994

* cited by examiner

*Primary Examiner*—Hezron Williams
*Assistant Examiner*—Rodney Frank
(74) *Attorney, Agent, or Firm*—Nixon & Vanderhye P.C.

(57) ABSTRACT

A liquid level detecting apparatus has an ultrasonic sensor, a reflector, a first pipe and a second pipe. The reflector reflects an ultrasonic wave from the ultrasonic sensor to a liquid level, and the ultrasonic sensor detects a reflection wave reflected on the liquid level to detect a liquid level position. The first and second pipe surrounds the ultrasonic wave transmission path from the ultrasonic sensor via the reflector to the liquid level. The first pipe and the second pipe are integrally configured and supported on a bottom of a tank to be rotatable about the first pipe.

7 Claims, 9 Drawing Sheets

LIQUID LEVEL DETECTING APPARATUS

CROSS REFERENCE TO RELATED APPLICATIONS

This application is based upon and claims the benefit of priority of Japanese Patent Application No. 2005-001910 filed on Jan. 6, 2005, the content of which are incorporated herein by reference.

FIELD OF THE INVENTION

The present invention relates to a liquid level detecting apparatus for detecting a liquid level of liquid within a tank, and it is well suited for use in, for example, detecting the liquid level of fuel within a fuel tank mounted on an automobile.

BACKGROUND OF THE INVENTION

As a conventional liquid level detecting apparatus for detecting a liquid level of a liquid in a tank, JP-06-249697-A, for example, discloses an apparatus that detects the liquid level with an ultrasonic wave. Specifically, the apparatus is for installing in a fuel tank mounted on an automobile. In the apparatus, an ultrasonic wave generated by an ultrasonic oscillation device is transmitted in fuel to the liquid level, the ultrasonic oscillation device receives a reflection wave reflected on the liquid level, and the liquid level is calculated based on the detection result of the reflection wave.

Further, U.S. Pat. No. 6,941,808, for example, discloses another liquid level detecting apparatus that is integrally formed with a fuel pump, which is installed in a fuel tank to feed fuel outward from the fuel tank. In the liquid level detecting apparatus according to U.S. Pat. No. 6,941,808, one end of an arm is rotatably supported on a bottom portion of the fuel tank, and the other end of the arm holds an ultrasonic oscillation device, so that the arm and the ultrasonic oscillation device can be retracted in the fuel pump.

According to this construction, in installing the liquid level detecting apparatus in the fuel tank, the liquid level detecting apparatus is inserted through an opening portion formed in the fuel tank in a state that the arm and the ultrasonic oscillation device are retracted in the fuel tank. Then, by installing the fuel pump on a predetermined position in the fuel tank to come in contact with a bottom face of the fuel tank, the arm flips upward to be extended, to return the liquid level detecting apparatus to a predetermined service position.

Ordinarily, the liquid level detecting apparatus is installed in the fuel tank through the opening portion of the fuel tank that is provided for installing the fuel pump, to decrease the number of the opening portion formed on the fuel tank.

Recent vehicle design is diversified, to make the shape of the fuel tank from simple rectangular one to complicated three-dimensional one. Accordingly, relative positions of the liquid level detecting apparatus and the fuel pump in the fuel tank is also diversified.

However, in the liquid level detecting apparatus according to U.S. Pat. No. 6,941,808, the relative positions of the liquid level detecting apparatus and the fuel pump is limited, because the liquid level detecting apparatus has a construction to be retractable in the fuel pump. That is, the liquid level detecting apparatus according to U.S. Pat. No. 6,941,808 cannot be applied to an apparatus that is disposed distant from the fuel pump by a specific length or more.

Further, the liquid level detecting apparatus is formed to be retractable in the fuel tank, so that an outer size of the fuel pump increases, and the size of the opening portion of the fuel tank also increases.

Furthermore, in a case that the liquid level detecting apparatus is installed at a position distant from the conventional opening portion of the fuel tank, it is necessary to form a base of the liquid level detecting apparatus in a large size, to make it difficult to install the liquid level detecting apparatus through the opening portion into the fuel tank.

SUMMARY OF THE INVENTION

The present invention is achieved in view of the above-mentioned issues, and has an object to provide a liquid level detecting apparatus that has flexibility in an installation position in a fuel tank without increasing a size of an opening portion formed on the fuel tank.

The liquid level detecting apparatus is for detecting a liquid level of a liquid in a liquid storage tank, and has: an ultrasonic oscillation device that generates an ultrasonic wave and receives a reflection wave of the ultrasonic wave reflected on the liquid level; a reflector member that reflects the ultrasonic wave generated by the ultrasonic oscillation device to the liquid level and reflects the reflection wave to the ultrasonic oscillation device; a first path member that has a tubular shape and surrounds a first transmission path of the ultrasonic wave between the ultrasonic oscillation device and the reflector member; a second path member that has a tubular shape and surrounds a second transmission path of the ultrasonic wave between the reflector member and the liquid level; a holder that holds the reflector member, the first path member and the second path member at predetermined positions relative to one another; and a base member that is to be fixed on a bottom of the liquid storage tank and supports the holder rotatably about a rotational axis in parallel with the first path member to fold the holder from an upright position to place the second path member on the second transmission path to a folded position to position closer to the bottom of the liquid storage tank than the upright position.

BRIEF DESCRIPTION OF THE DRAWINGS

Other features and advantages of the present invention will be appreciated, as well as methods of operation and the function of the related parts, from a study of the following detailed description, appended claims, and drawings, all of which form a part of this application. In the drawings:

DETAILED DESCRIPTION OF THE PREFERRED EMBODIMENTS

In each of the following embodiments, the liquid level detecting apparatus according to the present invention is adopted as a fuel level detecting apparatus for detecting a fuel level position in a fuel tank of an automobile.

First Embodiment

Figure 1:
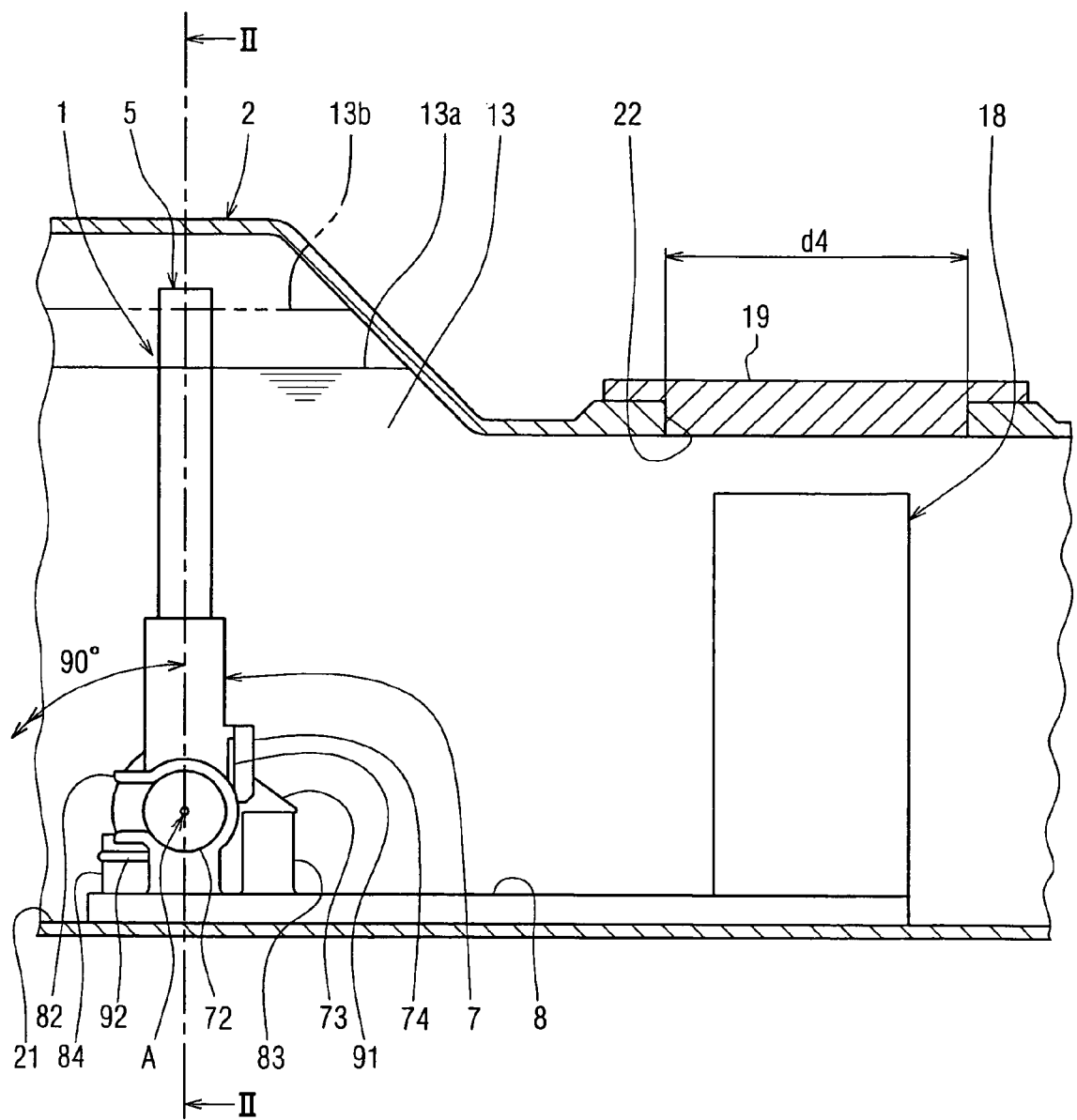
FIG. 1 is a partial cross-sectional view of a fuel tank provided with a liquid level detecting apparatus according to a first embodiment of the invention.
Figure 2:
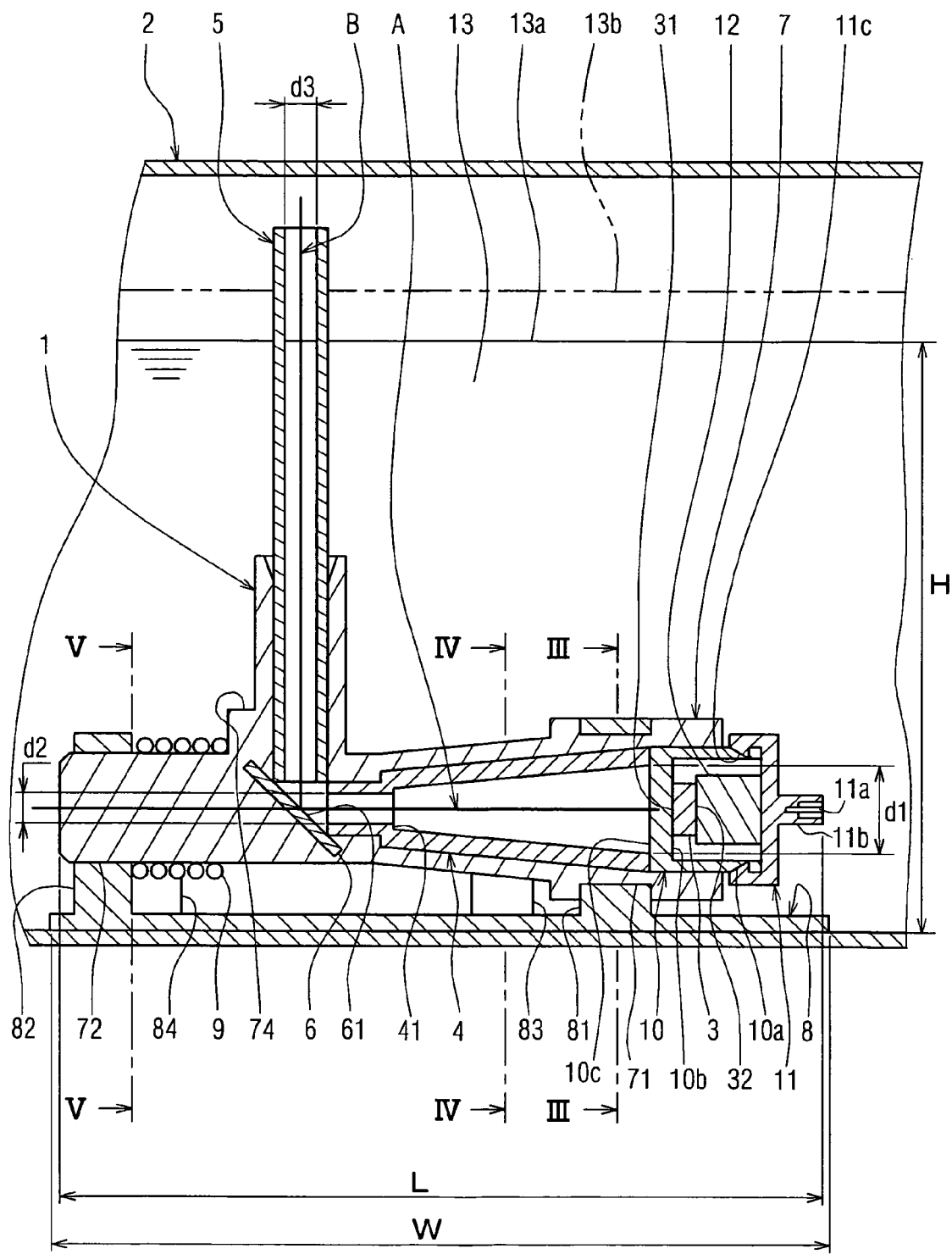
FIG. 2 is a cross-sectional view of the fuel tank and the liquid level detecting apparatus taken along a line II-II in FIG. 2.
Figure 3:
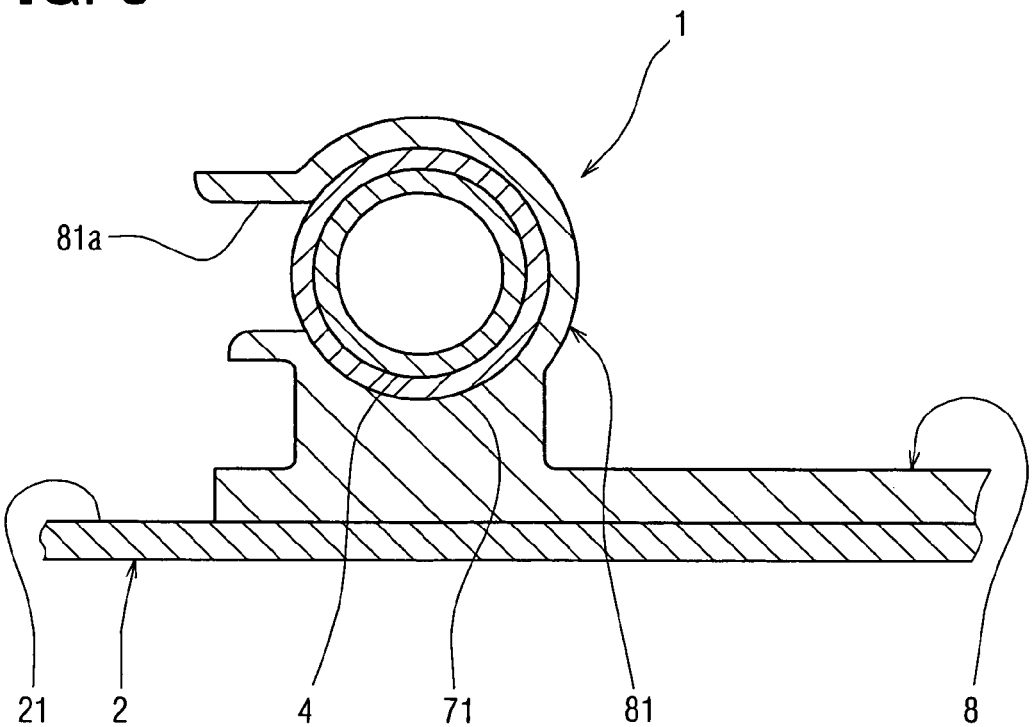
FIG. 3 is a cross-sectional view of the fuel tank and the liquid level detecting apparatus taken along a line III-III in FIG. 2.
Figure 4:
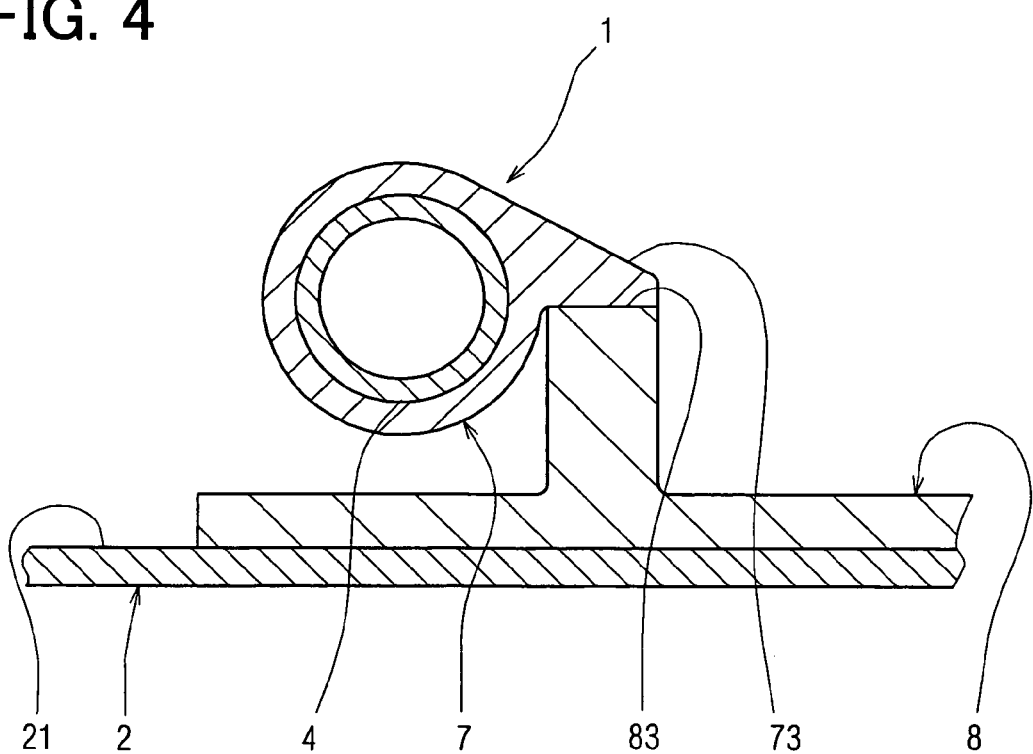
FIG. 4 is a cross-sectional view of the fuel tank and the liquid level detecting apparatus taken along a line IV-IV in FIG. 2.
Figure 5:
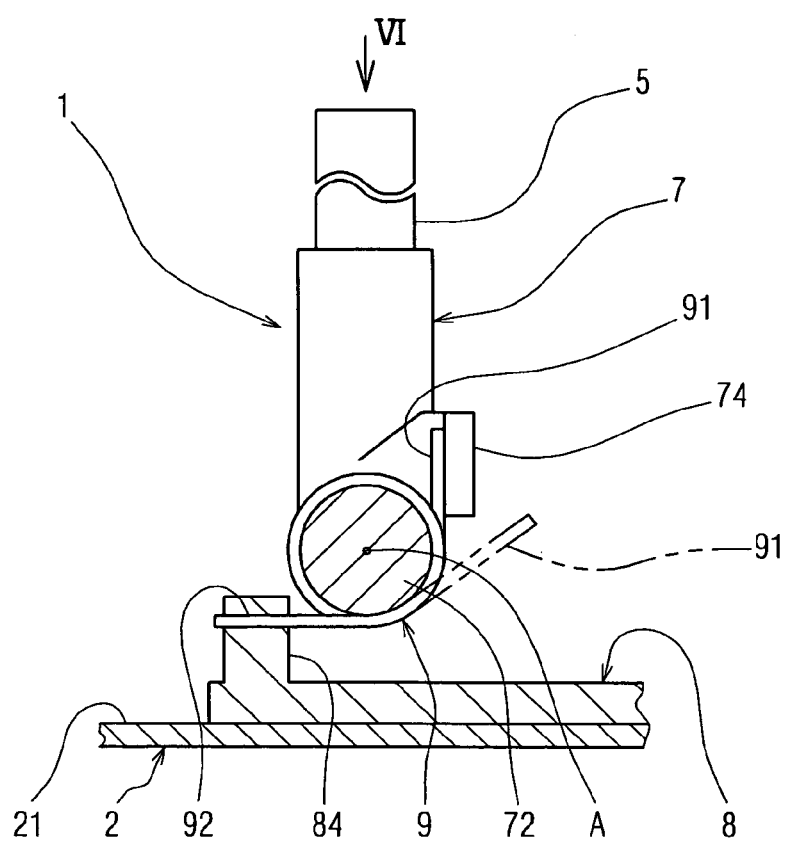
FIG. 5 is a cross-sectional view of the fuel tank and the liquid level detecting apparatus taken along a line V-V in FIG. 2.
Figure 6:
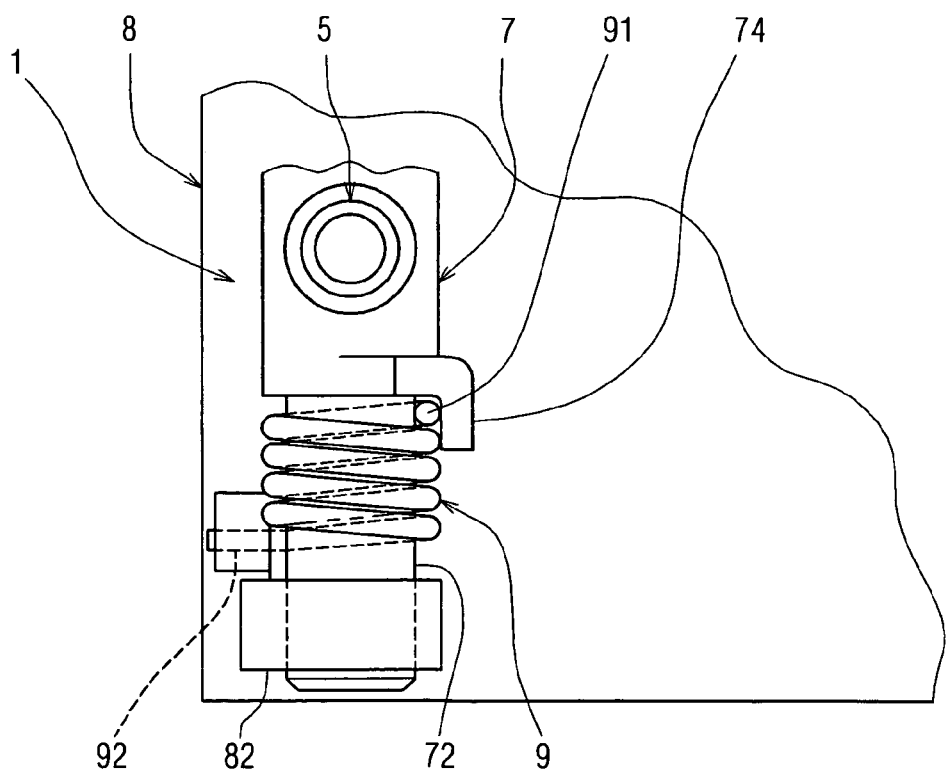
FIG. 6 is a view seen along an arrow VI in FIG. 5.
Figure 7:
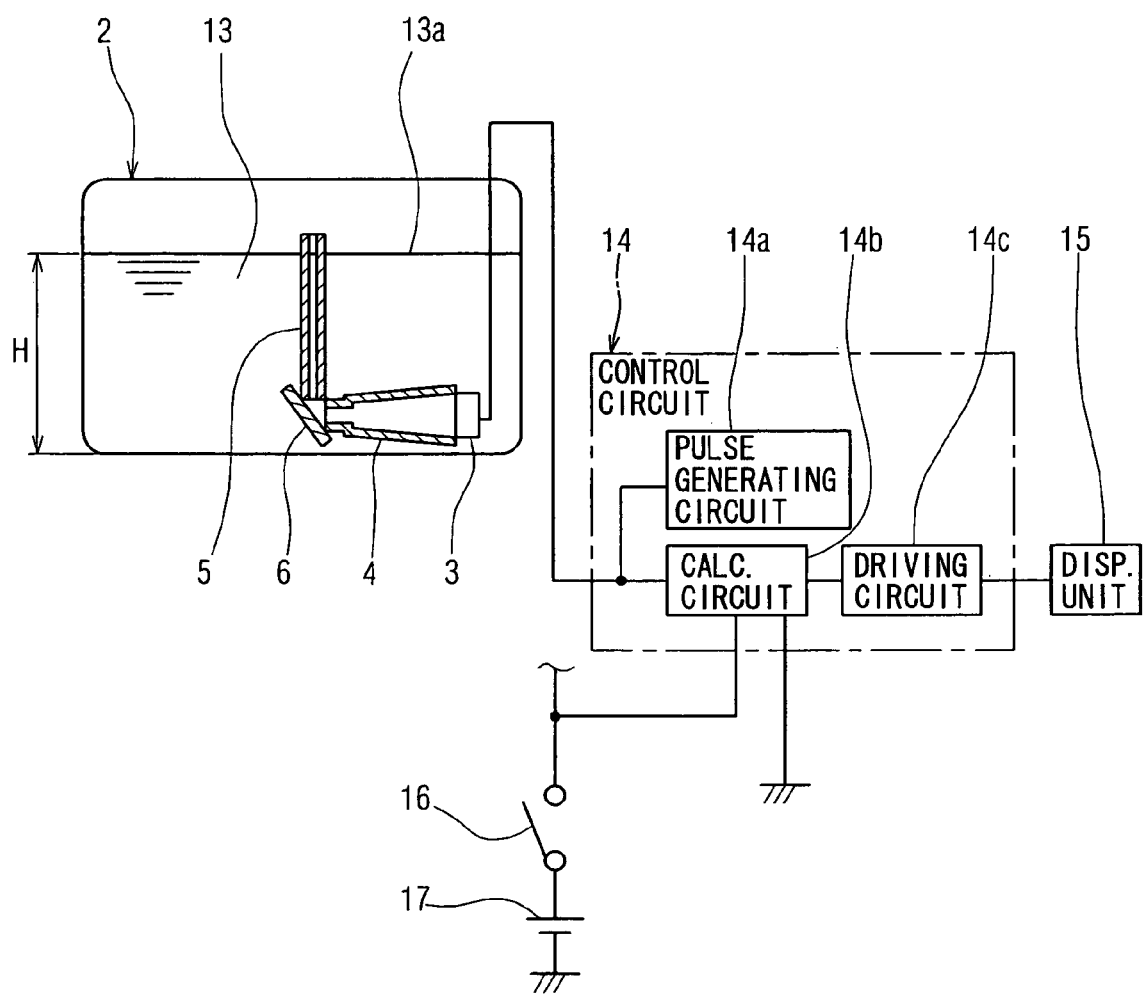
FIG. 7 is a schematic diagram showing an electric circuit construction in the liquid level detecting apparatus according to the first embodiment of the present invention.

FIG. 1 depicts a principal portion of the fuel tank 2 in which the fuel level detecting apparatus 1 is installed. A vertical direction in FIG. 1 corresponds with a vertical direction of the automobile. FIG. 2 depicts a cross-section of the fuel tank 2 and the fuel level detecting apparatus 1. FIGS. 3 to 5 respectively depict principal portions of the fuel level detecting apparatus 1. FIG. 6 is a partial top view of the fuel level detecting apparatus 1. FIG. 7 schematically depicts a circuit construction of the fuel level detecting apparatus 1.

As shown in FIG. 2, the fuel level detecting apparatus 1 includes an ultrasonic sensor 3, a guide pipe 4, a reflector plate 6 and a guide pipe 5, which respectively serve as the ultrasonic oscillation device, the first path member, a reflector member and a second path member according to the present invention. The ultrasonic sensor 3, the guide pipe 4, the reflector plate 6 and the guide pipe 5 are integrally installed in and supported by a housing 7. Further, the housing 7 is supported by a base 8, which serves as the base member according to the present invention. As shown in FIG. 2, the fuel level detecting apparatus 1 is fixed via the base 8 on a bottom face 21 of the fuel tank 2. As shown FIG. 1, a fuel pump 18, which corresponds to the equipment according to the present invention, is fixed on the base 8. The fuel pump 18 is installed in the fuel tank 2 to deliver the fuel 13 in the fuel tank 2 to an outer component such as engine.

That is, the fuel level detecting apparatus 1 is merged with the fuel pump 18 so as to decrease a man-hour needed to install the fuel level detecting apparatus 1 and the fuel pump 18 onto the fuel tank 2.

In the following is described a construction of the fuel level detecting apparatus 1 according to a first embodiment of the present invention.

The ultrasonic sensor 3, which serves as the ultrasonic oscillation device according to the present invention, is formed into a disk shape from a substance having a piezoelectric effect (an effect to change a volume in response to applied voltage and to generate a voltage in response to applied mechanical stress) such as PZT (lead titanate zirconate). On a front face 31 and a rear face 32 of the ultrasonic sensor 3 are formed electrodes (not shown), on which one end of a terminal 11a is soldered to connect the ultrasonic sensor 3 to an outer electric circuit. The ultrasonic sensor 3 oscillates in its thickness direction (horizontal direction in FIG. 2) due to the above-mentioned piezoelectric effect to produce an ultrasonic wave when a voltage is placed between the electrodes. When an ultrasonic wave enters to oscillate the ultrasonic sensor 3, it develops a voltage between the electrodes of the ultrasonic sensor 3. The ultrasonic sensor 3 is installed in and supported by a bracket 10.

The bracket 10 is formed into a substantially cylindrical shape with a bottom from resin or metal. The ultrasonic sensor 3 is in contact with a bottom portion 10b in the bracket 10. As shown in FIG. 2, a cover 11 is fixed on an opening end (right end in FIG. 2) of the bracket 10. A cushion member 12 is disposed between the rear face 32 of the ultrasonic sensor 3 and the cover 11 in the bracket 10.

The cover 11 is formed from a resinous material, for example, and fixed to the bracket 10 by engaging its engaging hook 11c with an engaging hole 10a of the bracket 10, as shown in FIG. 2. The other end of the terminal 11a protrudes from an outer surface of the cover 11, and a connector portion 11b is formed at the other end of the terminal 11a. The connector portion 11b is connected to a connector (not shown) that is fixed on a leading end of a lead wire extended from the outer electric circuit, to connect the ultrasonic sensor 3 to the outer electric circuit.

The cushion member 12 is formed from soft resinous material or rubber material. In the fuel level detecting apparatus 1 according to the first embodiment of the present invention, the cushion member 12 is formed from nitrile rubber. A relaxed length of the cushion member 12 alone in its longitudinal direction (horizontal direction in FIG. 2) is set larger than a distance between the ultrasonic sensor 3 and the cover 11 fixed onto the bracket 10. Thus, the ultrasonic sensor 3 and the cushion member 12 are inserted side by side into the bracket 10, then the cover is fixed onto the bracket 10, so that the cushion member 12 is pressurized and elastically deformed. The ultrasonic sensor 3 is pushed onto the bottom portion 10b by the elastic force, to be fixed at a specific position in the bracket 10. The cushion member 12 serves a function to absorb an ultrasonic pulse that leaks to a rear side (rightward in FIG. 2) from the ultrasonic sensor 3. Accordingly, the ultrasonic pulse developed by the ultrasonic sensor 3 is transmitted only leftward in FIG. 2 into the guide pipe 4, which corresponds to the first path member of the present invention.

The guide pipe 4 is formed from metallic material to form a transmission path of the ultrasonic wave between the ultrasonic sensor 3 and a reflector plate 6, which serves as a reflector member according to the present invention as described later. In the fuel level detecting apparatus 1 according to the first embodiment of the present invention, the guide pipe 4 is formed from die-cast aluminum alloy. One end portion (right end portion in FIG. 2) of the guide pipe 4 is in contact with the bracket 10 that supports the ultrasonic sensor 3. As shown in FIG. 3, the guide pipe 4 as a circular cross-section in a direction perpendicular to its longitudinal axis A. A diameter of the guide pipe 4 gradually decreases from d1 at its one end at the side of the ultrasonic sensor 3 (right end in FIG. 2) to d2 at the other end at the side of the reflector plate 6 (left end in FIG. 2). That is, a cross-sectional area or the diameter of the guide pipe 4 taken perpendicularly to the longitudinal axis A gradually decreases as going leftward in FIG. 2 from the ultrasonic sensor 3 to the reflector plate 6. As shown in FIG. 2, d1 is larger than d2. As shown in FIG. 2, a step 41 is formed in the guide pipe 4. The step 41 is formed into a ring shape, to face the ultrasonic sensor 3 as shown in FIG. 2. Accordingly, a part of the ultrasonic wave developed by the ultrasonic sensor 3 and transmitted in the guide pipe 4 enters the step 41. The ultrasonic wave is reflected by the step 41 toward the ultrasonic sensor 3, then enters the ultrasonic sensor 3.

At the other end portion (left end portion in FIG. 2) of the guide pipe 4, which is opposite from the ultrasonic sensor 3, is disposed the reflector plate 6, which reflects the ultrasonic wave developed by the ultrasonic sensor 3 toward a liquid level 13a of the fuel 13 in the fuel tank 2, as shown in FIG. 2. The reflector plate 6 is formed from metallic material. In the fuel level detecting apparatus 1 according to the first embodiment of the present invention, the reflector plate 6 is formed from steel metal such as stainless steel plate. The reflector plate 6 reflects the ultrasonic wave, which is developed by the ultrasonic sensor 3 and entering from a right-hand side thereof in FIG. 2, toward the liquid level 13a. That is, the reflector plate 6 is installed so change a transmission direction of the ultrasonic wave from a direction along the longitudinal axis A of the guide pipe 4 to a direction to enter the liquid level 13a at an incidence angle of 0 degree, that is, to a direction perpendicular to the liquid level 13a. That is, the reflective surface 61 is inclined by 45 degrees to the liquid level 13a. Accordingly, the liquid level 13a reflects the ultrasonic wave to transmit that on a path, on which the ultrasonic wave is once transmitted toward the liquid level 13a, so that the ultrasonic wave enters the reflector plate 6 again. Thus, it is possible to decrease an energy loss of the reflected ultrasonic wave from the liquid level 13a to an irreducibly minimum value, to increase a signal detection level of the reflected ultrasonic wave by the ultrasonic sensor 3 so as to improve liquid level detection accuracy.

The guide pipe 5 is formed from a metallic material into a cylindrical shape to form a transmission path of the ultrasonic wave between the reflector plate 6 and the liquid level 13a. In the fuel level detecting apparatus 1 according to the first embodiment of the present invention, the guide pipe 5 is formed from stainless steel pipe. As shown in FIG. 2, the guide pipe 5 is disposed so that its longitudinal axis B is perpendicular to the liquid level 13a, to set the incidence angle of the ultrasonic wave, which is reflected by the reflector plate 6 and transmitted into the liquid level 13a, to 0 degree as described above. The guide pipe 5 has a circular cross-section in a direction perpendicular to its longitudinal axis B, and a constant diameter d3 over its entire longitudinal length. The diameter d3 of the guide pipe 5 is substantially equal to the diameter d2 of the guide pipe 4 at the reflector plate 6 side end thereof. As shown in FIG. 2, the leading end position of the guide pipe 5 at the side of the liquid level 13a is set to protrude by a specific length over a maximum liquid level 13b of the fuel 13 in the fuel tank 2.

The above-mentioned bracket 10 that supports the ultrasonic sensor 3, the guide pipe 4, the reflector plate 6 and the guide pipe 5 are fitted in the housing 7. In the fuel level detecting apparatus 1 according to the first embodiment of the present invention, the housing 7 is formed from resinous material, specifically from a material having a fine chemical stability against the fuel 13 in the fuel tank 2. The housing 7 serves a function to support the above-mentioned elements to keep them at highly precise relative positions.

The housing 7 is rotatably supported by the base 8, which serves as a base member according to the present invention, as described later. The base 8 is fixed on the bottom face 21 of the fuel tank 2, so that the fuel level detecting apparatus 1 is fixed relative to the fuel tank 2. The housing 7 is rotatably supported by the base 8 about the longitudinal axis A, which is the center axis of the guide pipe 4. Accordingly, as shown in FIG. 2, a shaft portion 71 and a shaft portion 72 are formed in the housing 7. The shaft portion 71 and the shaft portion 72 are respectively coaxially formed to the longitudinal axis A of the guide pipe 4. The housing 7 is further provided with a stopper 73, which serves as the stopper means according to the present invention to stop the housing 7 at its service position and angle. As shown in FIG. 4, the stopper 73 extends outward from a portion of the housing 7 corresponding to the guide pipe 4. As shown in FIG. 4, the stopper 73 is in contact with a stopper receiver 83, which is formed on the base 8 to serves as the stopper means according to the present invention. The housing 7 is stopped at its service position, that is, at the position to make the longitudinal axis B of the guide pipe 5 perpendicular to the liquid level 13a.

As shown in FIG. 2, a return spring 9 is disposed around an outer circumference of the shaft portion 72 of the housing 7 to be coaxial to the shaft portion 72. The return spring 9 is an urging means according to the present invention that applies a torque to the housing 7 toward the above-mentioned service angle. The return spring 9 is a torsion coil spring formed from a steel wire made of spring steel and the like. As shown in FIG. 5, a spring end portion 91, which is one end of the return spring 9, is in contact with a spring receiver 74, which is formed in the housing 7. As shown in FIG. 5, a spring end portion 92, which is the other end of the return spring 9, is in contact with and supported by a spring receiver 84, which is formed on the base 8. In a relaxed state of the return spring 9, the spring end portion 91 is at an angle indicated by a broken line in FIG. 5. Thus, in installing the return spring 9 on the housing 7 and the base 8, the return spring 9 is twisted counterclockwise in FIG. 4. Accordingly, when the return spring 9 is installed on the housing 7 and the base 8, the return spring 9 generates the elastic force to return to its relaxed position. That is, in FIGS. 4 and 5, the return spring 9 applies a torques to the housing 7 to rotate the housing 7 clockwise about the longitudinal axis A. As shown in FIG. 4, the torque brings the stopper 73 of the housing 7 to the stopper receiver 83, which is formed on the base 8 to serve as the stopper means according to the present invention, to keep the housing 7 at its service position and angle.

In the fuel level detecting apparatus 1 according to the first embodiment of the present invention, the base 8 is formed from resinous material having a fine chemical stability against the fuel 13 in the fuel tank 2, as the housing 7 is. A shaft-receiving portion 81 and a shaft-receiving portion 82 are formed on the base 8 to rotatably support the housing 7. That is, as shown in FIG. 2, the shaft-receiving portion 81 is rotatably engaged with the shaft portion 71, and the shaft-receiving portion 82 is rotatably engaged with the shaft portion 72. As shown in FIG. 3, the shaft-receiving portion 81 is provided with an opening portion 81a, to open partially in a circumferential direction thereof. Accordingly, in installing the bracket 7 on the base 8, it is possible to fit the shaft portion 71 via the opening portion 81a to the shaft-receiving portion 81. In this regard, an inner diameter of the shaft-receiving portion 81 of the base 8 alone, in a state that it is not fitted to the shaft portion 71, is substantially equal to or slightly smaller than an outer diameter of the shaft portion 71. Thus, when the shaft portion 71 is fitted to the shaft-receiving portion 81, the shaft-receiving portion 81 is slightly elastically deformed, and the elastic force acts as a friction force against a rotation of the shaft portion 71. In an analogous fashion, an opening portion 82a is formed in the shaft-receiving portion 82 to install the shaft portion 72 thereon, and a relation between an inner diameter of the shaft-receiving portion 82 and an outer diameter of the shaft portion 72 is set as the shaft-receiving portion 81 and the shaft portion 71.

As shown in FIG. 4, the base 8 is provided with the stopper receiver 83, which serves as the stopper means to come in contact with the stopper 73 of the housing 7 to stop the housing 7 at its service position and angle.

As shown in FIG. 5, the base 8 is provided with the spring receiver 84 that receives the spring end portion 92 of the return spring 9.

On the base 8 is fixed the fuel pump 18, which serves as the equipment according the present invention. The fuel pump 18 is a dynamo-electrically driven pump, to feed the fuel 13 in the fuel tank 2 to a fuel injection apparatus provided in an engine, for example. That is, on the base 8 are fixed the fuel level detecting apparatus 1 and the fuel pump 18 side by side. Accordingly, it is possible to fix two elements of the fuel level detecting apparatus 1 and the fuel pump 18 by fastening one element of the base 8 to the bottom face 21 of the fuel tank 2, to improve a workability to install the elements in the fuel tank 2.

In the following is described an electric circuit construction of the fuel level detecting apparatus 1 according to the first embodiment of the present invention referring to FIG. 7.

As shown in FIG. 7, a control circuit 14 is connected via an ignition switch 16 to a battery 17. The ultrasonic sensor 3 is connected to the control circuit 14. Further, a display unit 15 is connected to the control circuit 14.

The control circuit 14 is formed from a microcomputer and the like, to include a pulse generating circuit 14a that applies a pulse voltage signal to the ultrasonic sensor 3, a calculation circuit 14b that processes a reflection wave receiving signal outputted by the ultrasonic sensor 3 and calculates the liquid level based on the reflection wave receiving signal, and a driving circuit 14c that outputs a driving signal to drive the display unit 15 based on a liquid level signal calculated by the calculation circuit 14b. An electric power is supplied from the battery 17 to the control circuit 14 by turning on the ignition switch 16, and the fuel level detecting apparatus 1 starts operating.

The display unit 15 is formed from a pointer instrument, a liquid crystal display, and so on, and installed in a combination meter (not shown) in front of a driver's seat in the automobile. The display unit 15 is driven by the driving circuit 14c of the control circuit 14, to display the position of the liquid level 13a calculated by the calculation circuit 14b, that is, a residual quantity of the fuel 13 in the fuel tank 2, to be visible to the driver.

In the following is described a fuel level detecting operation by the fuel level detecting apparatus 1 according to the first embodiment of the present invention.

The pulse generating circuit 14a applies the pulse voltage signal to the ultrasonic sensor 3, and the ultrasonic sensor 3 develops an ultrasonic pulse and transmits the ultrasonic pulse to the fuel 13 in the fuel tank 2. Then, an oscillation face 31 of the ultrasonic sensor 3 oscillates, and the oscillation of the oscillation face 31 is transmitted to the bottom portion 10b of the bracket 10. Further, an ultrasonic wave is transmitted from an outer face 10c of the bracket 10 into the fuel 13. A part of the ultrasonic wave is transmitted in the guide pipe 4 to enter the step 41, and reflected by the step 41 to enter the oscillation face 31 of the ultrasonic sensor 3 again. Concurrently, a part of the ultrasonic pulse developed by the ultrasonic sensor 3 toward the fuel 13 is transmitted in the guide pipe 4 to enter the reflective surface 61. Then, the ultrasonic pulse is reflected by the reflective surface 61 to be further transmitted in the guide pipe 5 toward the liquid level 13a. The ultrasonic pulse is reflected on the liquid level 13a, and transmitted on the path, on which the ultrasonic pulse is once transmitted toward the liquid level 13a, that is, transmitted via the guide pipe 5, the reflective surface 61, and the guide pipe 4 to enter the ultrasonic sensor 3 again.

That is, the ultrasonic sensor 3 develops one ultrasonic pulse by being driven by the pulse generating circuit 14a, and then receives two reflection waves from the step 41 and from the liquid level 13a as described above, in accordance with the one ultrasonic pulse. As shown in FIG. 2, a transmission path from the ultrasonic sensor 3 to the step 41 is shorter than a transmission path from the ultrasonic sensor 3 to the liquid level 13a, so that the ultrasonic sensor 3 receives the reflection pulse from the step 41 first, and then receives the reflection pulse from the liquid level 13a. The ultrasonic sensor 3 generates voltage signals every time when it receives these reflection pulses, and then the voltage signals are inputted into the calculation circuit 14b.

The calculation circuit 14b calculates a period from when the pulse generating circuit 14a generates the pulse voltage signal to when the pulse generating circuit 14a detects the first reflection pulse, and a period from when the pulse generating circuit 14a generates the pulse voltage signal to when the pulse generating circuit 14a detects the second reflection pulse.

In this regard, the step 41 is positioned at a predetermined position relative to the ultrasonic sensor 3. That is, a distance between the step 41 and the ultrasonic sensor 3 is known. Thus, the calculation circuit 14b calculates a transmission speed of the ultrasonic pulse in the fuel 13 based on the period from when the pulse generating circuit 14a generates the pulse voltage signal to when the pulse generating circuit 14a detects the first reflection pulse from the step 41, and the distance between the step 41 and the ultrasonic sensor 3. Then, the calculation circuit 14b calculates the position of the liquid level 13a, that is, a height H of the liquid level 13a in FIG. 2, based on the transmission speed of the ultrasonic pulse in the fuel 13, which is calculated as described above, and the period from when the pulse generating circuit 14a generates the pulse voltage signal to when the pulse generating circuit 14a receives the reflection pulse from the liquid level 13a. Further, the calculation circuit 14a calculates the residual quantity of the fuel 13 in the fuel tank 2, based on a shape of the fuel tank 2, which is memorized in advance.

The driving circuit 14c outputs a driving signal to the display unit 15 to display the height H of the liquid level 13a or the residual quantity of the fuel 13 that is calculated by the calculation circuit 14b, for example, to drive a pointer (not shown) to an angle in accordance with the height H of the liquid level 13a or the residual quantity of the fuel 13. Accordingly, the display unit 15 displays the height H of the liquid level 13a or the residual quantity of the fuel 13 in the fuel tank 2.

In the following is described a feature of the fuel level detecting apparatus 1 according to the first embodiment of the present invention, specifically an effect by the construction that: the housing 7 is rotatably supported about the longitudinal axis A, which is the center axis of the guide pipe 4; the stopper 73 and the stopper receiver 83 stop the housing 7 at its service position and angle; and the urging force of the return spring 9 keeps the housing 7 at the service position and angle.

In installing the fuel level detecting apparatus 1 according to the first embodiment of the present invention in the fuel tank 2, the fuel level detecting apparatus 1 is placed in the fuel tank 2 through an opening portion 22 that is provided in the fuel tank 2. In this regard, the opening portion 22 has a circular shape and a diameter d4 larger than a width W of the base 8 to place the fuel level detecting apparatus 1 therethrough in the fuel tank 2. As shown in FIG. 1, a length L of the fuel level detecting apparatus 1 is smaller than the width W, and positioned inside an outline of the base 8.

As shown in FIG. 1, the fuel tank 2, in which the fuel level detecting apparatus 1 according to the first embodiment of the present invention is installed, has the opening portion 22 apart from a position where the maximum liquid level 13b appears.

In installing the fuel level detecting apparatus 1 into the fuel tank 2 through the opening portion 22 provided in the fuel tank 2, a leading end (left end in FIG. 1) of the base 8 at the side of the fuel level detecting apparatus 1 is inserted into the opening portion 22. The base 8 is gradually inserted into the fuel tank 2 until the fuel pump 18 is inserted into the opening portion 22 to complete to put the fuel level detecting apparatus 1 and the fuel pump 18 into the fuel tank 2.

As shown in FIG. 1, the fuel level detecting apparatus 1 according to the first embodiment of the present invention is approximately U-shaped in an insertion direction into the opening portion 22. Thus, in a case that the housing 7 is rigidly fixed to the base 8, not to rotate relative to the base 8, it is difficult or impossible to insert the fuel level detecting apparatus 1 into the fuel tank 2 through the opening portion 22. If the opening portion 22 is large to insert the fuel level detecting apparatus 1 into the fuel tank 2, a strength of the fuel tank 2 decreases.

As shown in FIG. 1, in the fuel level detecting apparatus 1 according to the first embodiment of the present invention, the housing 7 is rotatably supported by the base about the longitudinal axis A, which is the center axis of the guide pipe 4. Thus, the housing 7 can rotate anticlockwise by approximately 90 degrees about the longitudinal axis A.

Accordingly, in inserting the fuel level detecting apparatus 1 through the opening portion 22 into the fuel tank 2, the housing 7 can be held manually or by an assembly jig at a state rotated anticlockwise in FIG. 1. Thus, the fuel level detecting apparatus 8, which has the fuel pump 18 fixed on the base 8, is approximately L-shaped, to be easily inserted through the opening portion 22 into the fuel tank 2.

After inserting the fuel level detecting apparatus 1 through the opening portion 22 into the fuel tank 2, the housing 7 is released from the held state manually or removing the assembly jig. Thus, the housing 7 rotates clockwise in FIG. 1 about the longitudinal axis A by the urging force of the return spring 9, to be securely returned to the service position and angle shown in FIG. 1.

As described above, it is possible to put the fuel level detecting apparatus 1 into the fuel tank 2 without extending the size of the opening portion 22. In other words, it is possible to improve flexibility in installing the fuel level detecting apparatus 1 through the opening portion 22 into the fuel tank 2.

Conventional fuel level detecting apparatus is formed to be retractable in the fuel pump, so that the fuel level detecting apparatus can be easily inserted in the fuel tank by retracting the fuel level detecting apparatus in the fuel pump. However, relative positions of the liquid level detecting apparatus and the fuel pump is limited in the fuel level detecting apparatus, to retract the fuel level detecting apparatus in the fuel pump. That is, a distance between the fuel level detecting apparatus and the fuel pump is limited within a specific length to retract the fuel level detecting apparatus in the fuel pump. The limited relative positions of the fuel level detecting apparatus and the fuel pump in the fuel tank is not compatible with varied shapes of the fuel tank.

In the fuel level detecting apparatus 1 according to the first embodiment of the present invention, both of the housing 7 and the fuel pump 18 are fixed on the base 8. Thus, it is possible to determine the relative positions of the fuel level detecting apparatus 1 and the fuel pump 18 in the fuel tank 2 as needed by adequately selecting the shape of the base 8. Accordingly, it is possible to improve the installation flexibility of the fuel level detecting apparatus 1 relative to the shape and position of the opening portion 22 of the fuel tank 2.

Second Embodiment

Figure 8:
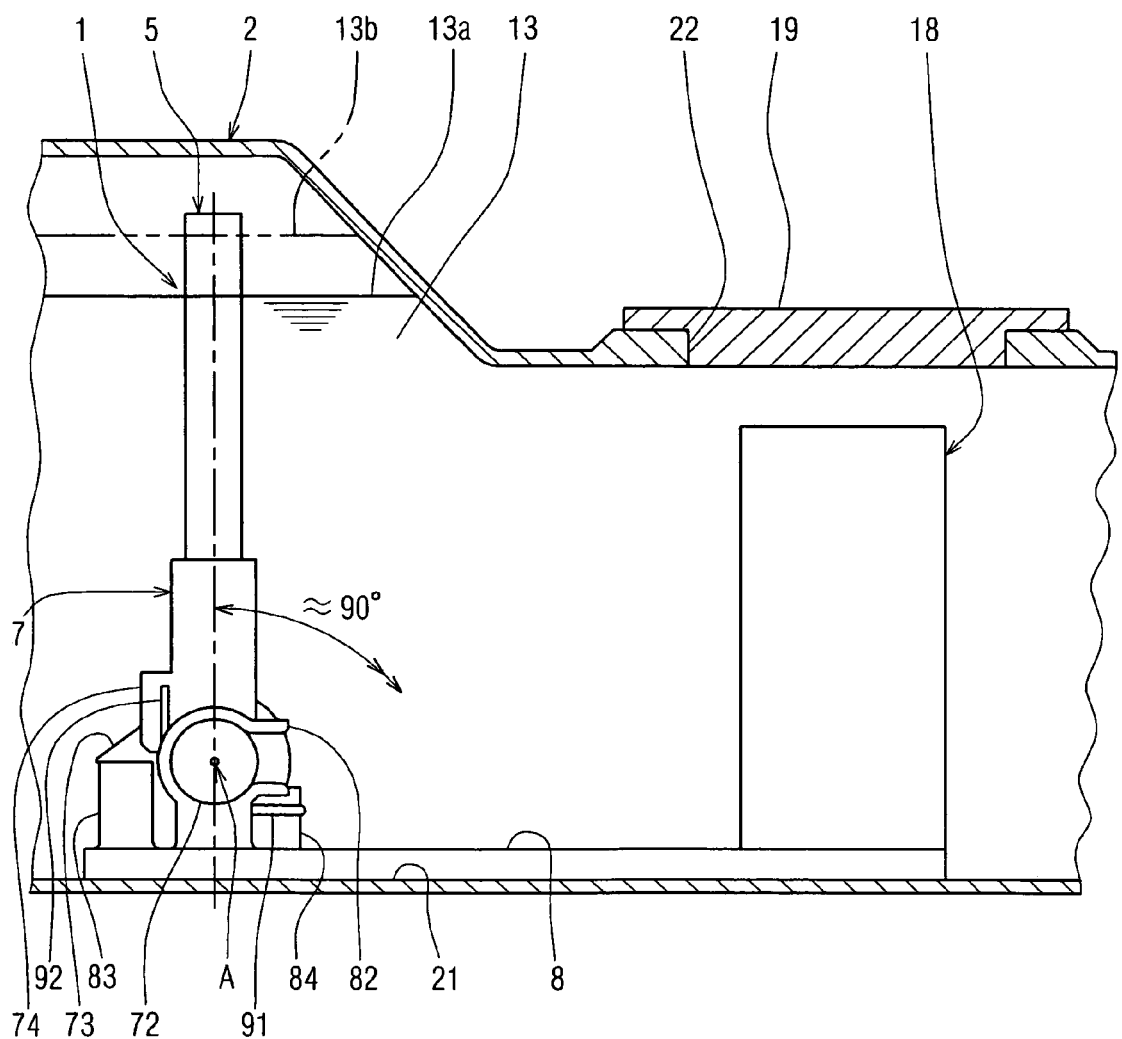
FIG. 8 is a partial cross-sectional view of a fuel tank provided with a liquid level detecting apparatus according to a second embodiment of the invention.

FIG. 8 depicts a principal portion of the fuel tank 2 in which a fuel level detecting apparatus 1 according to a second embodiment of the present invention is installed.

In the fuel level detecting apparatus 1 according to the second embodiment of the present invention, the housing 7 can rotate in an opposite direction from in the fuel level detecting apparatus 1 according to the first embodiment. That is, as shown in FIG. 8, the stopper 73 provided on the housing 7 and the stopper receiver 83 provided on the base 8 are positioned oppositely from those in the fuel level detecting apparatus 1 according to the first embodiment. Accordingly, the installation direction of the return spring 9, and the opening directions of the opening portion 81a of the shaft-receiving portion 81 and of the opening portion 82a of the shaft-receiving portion 82 are opposite from those in the fuel level detecting apparatus 1 according to the first embodiment.

Accordingly, in the fuel level detecting apparatus 1 according to the second embodiment of the present invention, in inserting the fuel level detecting apparatus 1 through the opening portion 22 into the fuel tank 2, the housing 7 is held manually or by an assembly jig in advance at a state rotated clockwise in FIG. 8. The fuel level detecting apparatus 1 is gradually inserted into the fuel tank 2 from a leading end of the base 8 at the side of the housing 7.

The fuel level detecting apparatus 1 according to the second embodiment of the present invention can be installed through the opening portion 22 into the fuel tank 2 as the fuel level detecting apparatus according to the first embodiment of the present invention.

Third Embodiment

Figure 9:
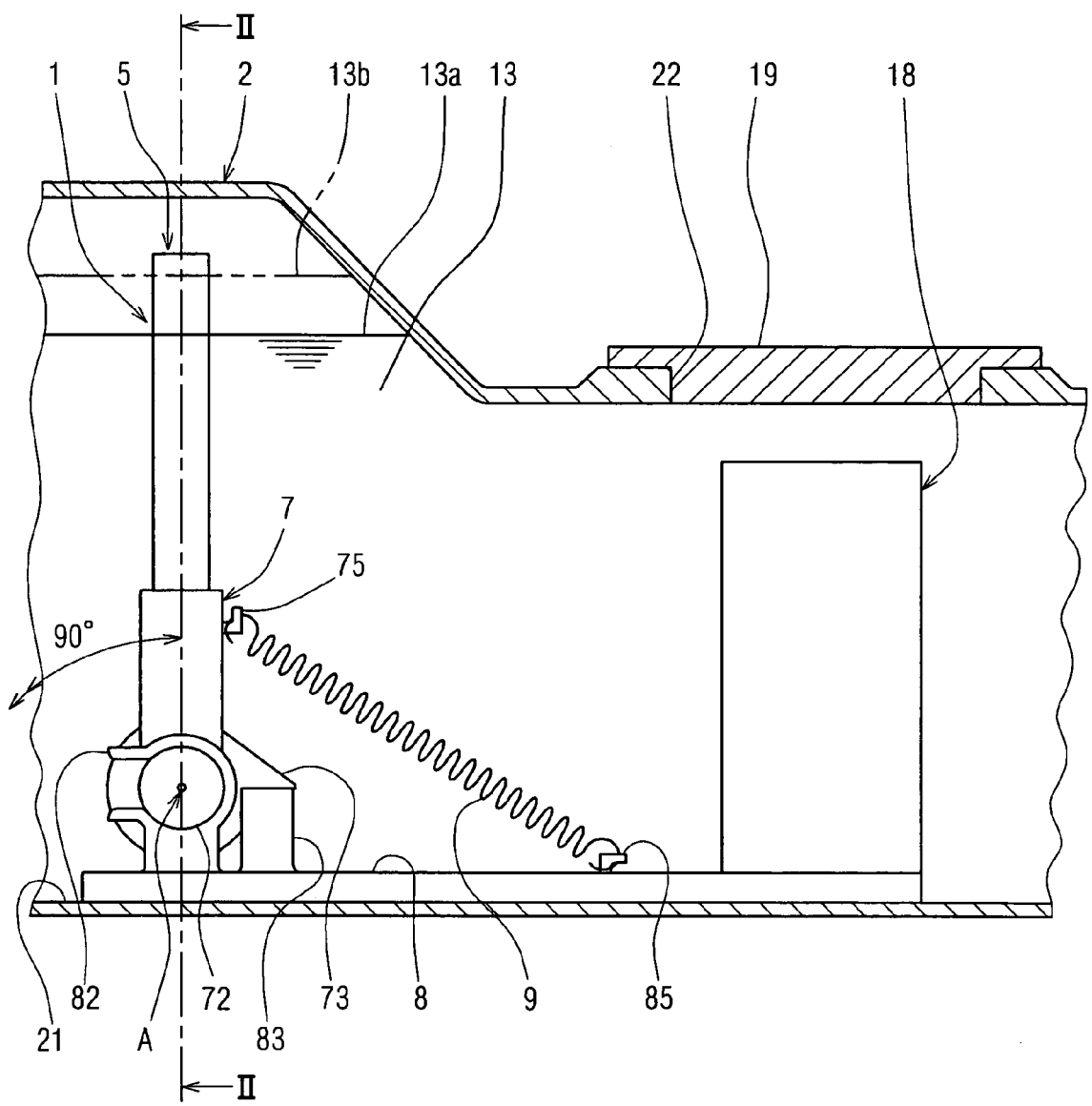
FIG. 9 is a partial cross-sectional view of a fuel tank provided with a liquid level detecting apparatus according to a third embodiment of the invention.

FIG. 9 depicts a principal portion of the fuel tank 2 in which a fuel level detecting apparatus 1 according to a third embodiment of the present invention is installed.

The fuel level detecting apparatus 1 according to the third embodiment of the present invention has a return spring 9 that has a different shape and installation position from those of the return spring 9 in the fuel level detecting apparatus 1 according to the first embodiment of the present invention. Specifically, the shape of the return spring 9 is a tension coil spring shown in FIG. 9 instead of the torsion coil spring in the fuel level detecting apparatus according to the first and second embodiments. Further, the housing 7 is provided with a spring hook 75 and the base 8 is provided with a spring hook 85, and both ends of the return spring 9 is hooked on the spring hooks 75, 85 as shown in FIG. 9 by stretching the return spring 9. Thus, the return spring 9 generates a torque to rotate the housing 7 clockwise about the longitudinal axis A. As shown in FIG. 9, the torque brings the stopper 73 of the housing 7 in contact with the stopper receiver 83 of the base 8, to keep the housing at its service position and angle.

In installing the fuel level detecting apparatus 1 according to the third embodiment of the present invention through the opening portion 22 in the fuel tank 2, the housing 7 is held manually or by an assembly jig at a state rotated clockwise in FIG. 9. Then, the base 8 is gradually inserted from a leading end portion at the side of the housing 7 in keeping the housing 7 in this state.

Accordingly, the fuel level detecting apparatus 1 according to the second embodiment of the present invention can be easily installed through the opening portion 22 into the fuel tank 2 as the fuel level detecting apparatus according to the first embodiment of the present invention.

Fourth Embodiment

Figure 10:
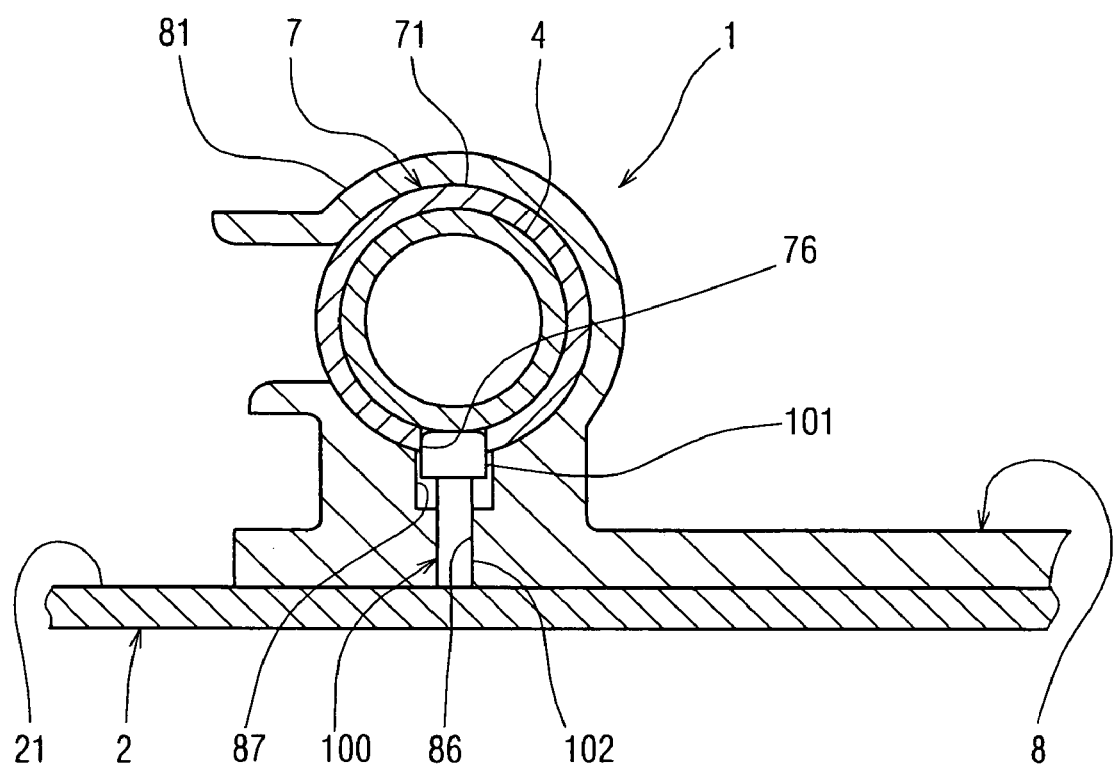
FIG. 10 is a cross-sectional view showing a shaft-receiving portion of a liquid level detecting apparatus according to a fourth embodiment of the present invention.

FIG. 10 depicts a cross-section of a shaft-receiving portion 81 of a fuel level detecting apparatus 1 according to a fourth embodiment of the present invention. FIG. 10 is taken along a line corresponding to the line III-III in FIG. 2, which depicts the fuel level detecting apparatus 1 according to the first embodiment of the present invention.

The fuel level detecting apparatus 1 according to the third embodiment of the present invention has a stopper means for stopping the housing 7 at its service position and angle, which has a different configuration from that in the fuel level detecting apparatus 1 according to the first embodiment of the present invention. Specifically, as shown in FIG. 10, the fuel level detecting apparatus 1 according to the fourth embodiment is provided with a lock pin 100, a through hole 76 of the housing 7 and a through hole 86 of the base 8, instead of the stopper 73 of the housing 7 and the stopper receiver 83 of the base 8.

The lock pin 100 is formed from resinous material or metal into a coaxially stepped cylindrical shape shown in FIG. 10. Specifically, the lock pin 100 has a large diameter portion 101 and a small diameter portion 102, which are coaxial to each other.

As shown in FIG. 10, the through hole 76 is formed at the shaft portion 71 of the housing 7. The through hole 76 has a diameter slightly larger than a diameter of the large diameter portion 101 of the lock pin 100 so as to be rigidly fitted to the large diameter portion 101 of the lock pin 100.

The shaft-receiving portion 81 of the base 8 is provided with the through hole 86 in the same manner that the housing 7 is provided with the through hole 76. The through hole 86 has a diameter slightly larger than a diameter of the small diameter portion 102 of the lock pin 100 so as to be rigidly fitted to the small diameter portion 102 of the lock pin 100. Further, the shaft-receiving portion 81 is provided with an allowance hole 87 at the side of the shaft portion 71 with respect to the through hole 86. The allowance hole 87 has a diameter that is sufficiently larger than the diameter of the large diameter portion 101 of the lock pin 100.

In the following are described actions and effects of the stopper means, that is, the lock pin 100, the through hole 76 and the through hole 86 in the fuel level detecting apparatus 1 according to the fourth embodiment of the present invention, in installing the fuel level detecting apparatus 1 in the fuel tank 2.

Figure 11:
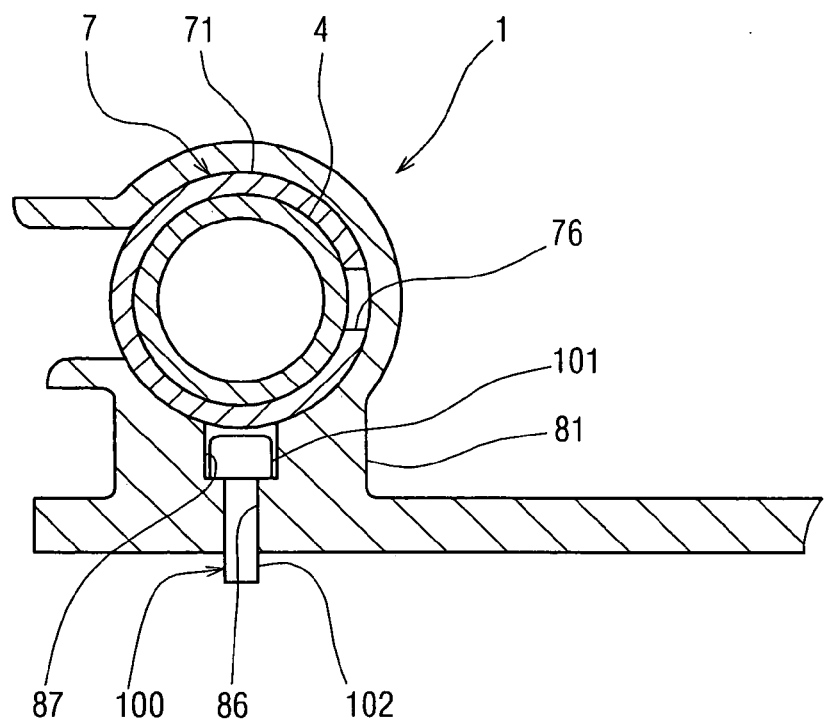
FIG. 11 is another cross-sectional view showing the shaft-receiving portion of the liquid level detecting apparatus according to the fourth embodiment of the present invention.

Firstly, the housing 7 is rotated manually or by an assembly jig anticlockwise in FIG. 1, and then the fuel level detecting apparatus 1 is gradually inserted into the opening portion 22 from the leading end portion of the base 8 at the side of the housing 7. At this time, in the shaft portion 71 of the housing 7 shown in FIG. 11, the lock pin 100 is at a lower position by its own weight and the through hole 76 is not aligned with the lock pin 100 in the state that the housing 7 is rotated.

Figure 12:
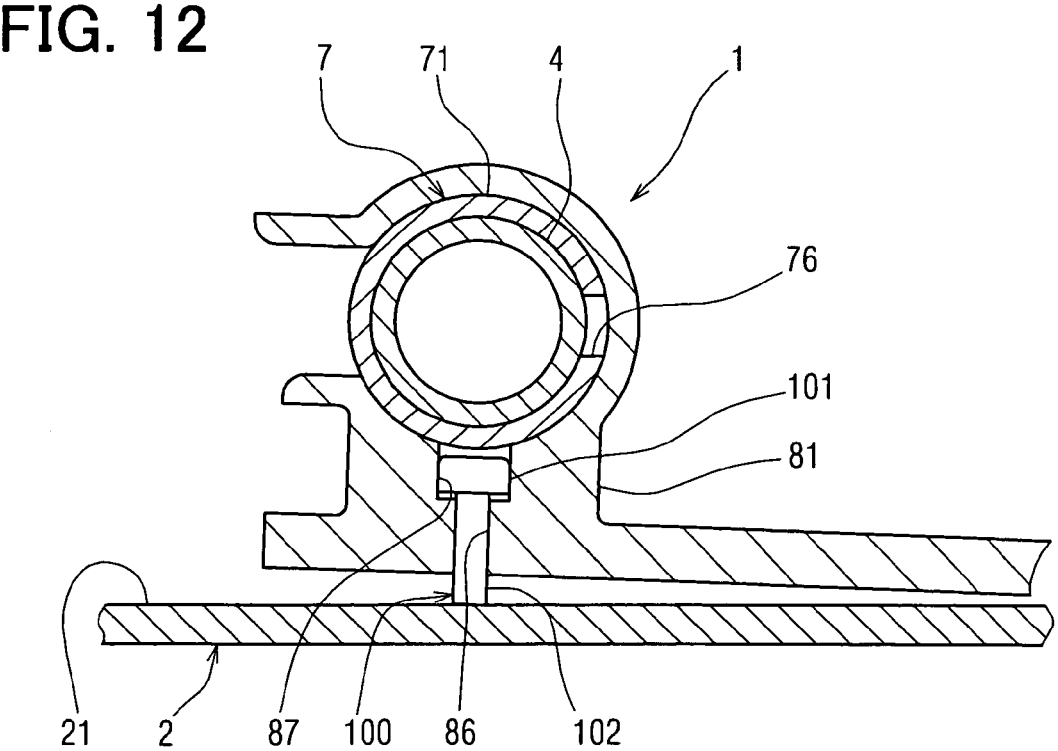
FIG. 12 is still another cross-sectional view showing the shaft-receiving portion of the liquid level detecting apparatus according to the fourth embodiment of the present invention.

The base 8 is completely inserted into the opening portion 22, and then the base 8 comes in contact with the bottom face 21 of the fuel tank 2 as shown in FIG. 12. In this time, the through hole 76 is still misaligned with the lock pin 100, so that the base 8 does not come in complete contact with the bottom face 21.

When the housing 7 is released from the held state manually or removing the assembly jig. Thus, the housing 7 rotates clockwise by the urging force of the return spring 9 to the service position and angle. When the housing 7 comes to its service position and angle, the through hole 76 of the housing 7 is aligned with the lock pin 100, and the large diameter portion 101 of the lock pin 100 is fitted to the through hole 76. Concurrently, the small diameter portion 102 of the lock pin 100 is taken into the base 8, and the base 8 comes in a tight contact with the bottom face 21 of the fuel tank 2, to complete installing the fuel level detecting apparatus 1 into the fuel tank 2.

In the fuel level detecting apparatus 1 according to the fourth embodiment of the present invention, when the fuel level detecting apparatus 1 is installed in the fuel tank 2, the large diameter portion 101 of the lock pin 100 is fitted to the through hole 76 of the housing 7, and the small diameter portion 102 of the lock pin 100 is fitted to the through hole 86 of the base 8, to prevent the housing 7 from rotating about the longitudinal axis A. Accordingly, in the fuel level detecting apparatus 1, even when a vibration in a traveling time of the automobile acts on the fuel tank 2, it is possible to keep positioning the housing 7 securely to its service position and angle. Accordingly, the fuel level detecting apparatus 1 can detect the fuel level position stably in the operating time of the automobile.

In the fuel level detecting apparatus 1 according to the fourth embodiment of the present invention is not provided with the stopper 73 and the stopper receiver 83 in the fuel level detecting apparatus 1 according to the first embodiment of the present invention. However, the fuel level detecting apparatus 1 according to the fourth embodiment of the present invention may be provided with the stopper 73 and the stopper receiver 83 in the fuel level detecting apparatus 1 according to the first embodiment of the present invention. In this case, the stopper 73 and the stopper receiver 83 serve a function to stop the housing 7 at its service position and angle, and the lock pin 100, the through hole 76 and the through hole 86 serve a function to keep the housing 7 at the service position and angle securely when the fuel tank 2 is vibrated.

In the above-described fuel level detecting apparatus 1 according to the first to fourth embodiments of the present invention, the housing 7 is configured to rotate about the longitudinal axis A, which is the center axis of the guide pipe 4. However, the axis of rotation of the housing 7 is not limited to the longitudinal axis A. Alternatively, the axis of rotation of the housing 7 may be set to an axis that is different from and in parallel with the longitudinal axis A.

In the above-described fuel level detecting apparatus 1 according to the first to fourth embodiments of the present invention, on the base 8 is fixed the fuel pump 18, which corresponds to the equipment according to the present invention, in addition to the fuel level detecting apparatus 1. However, the equipment is not limited to the fuel pump 18. Alternatively, other kinds of the equipment can be fixed on the base 8. Further, the number of the equipment fixed on the base 8 may be modified from one into two or more.

In the fuel level detecting apparatus 1 according to the first to fourth embodiments of the present invention, on the base 8 is fixed the fuel pump 18, which is the equipment according to the present invention. However, it is possible that no equipment other than the fuel level detecting apparatus 1 is fixed on the base 8. For example, in a case that the fuel level detecting apparatus 1 is positioned away from the opening portion 22 in the fuel tank 2, the length of the base 8 is large in an insertion direction to insert the base 8 into the opening portion 22. Thus, it is difficult to insert the fuel level detecting apparatus 1 into the fuel tank 2 through the opening portion 22, even when the fuel pump 18 is not fixed on the base 8. Accordingly, as described in the fuel detecting apparatus according to the first to fourth embodiments of the present invention, the fuel level detecting apparatus 1 can be easily inserted into the housing 7, be forming the housing 7 retractable.

The fuel level detecting apparatus 1 according to the first, second and fourth embodiments of the present invention has a torsion coil spring, and the fuel level detecting apparatus 1 according to the third embodiment of the present invention has a tension coil spring, to serve as the urging means according to the present invention. In every embodiment of the present invention, a coil spring is used for the urging means according to the present invention. However, the urging means is not limited to coil spring, and other kinds of spring such as a leaf spring and a volute spring may be used for the urging means. Further, the material of the urging means is not limited to metal, and resinous material and a rubber material may be used for the urging means.

In the fuel level detecting apparatus 1 according to the first to fourth embodiments of the present invention, the guide pipe 4 is formed from an aluminum die-cast alloy, and the guide pipe 5 is formed from stainless pipe. However, the material to form the guide pipe 4 is not limited to these kinds of metal, and other kinds of metal may be used for the guide pipe 4. For example, the guide pipe 4 may be formed from steel material, and the guide pipe 5 may be formed from aluminum pipe. Further, the guide pipe 4 and the guide pipe 5 may be formed from a material other than metal, such as resinous material, ceramic material; and so on. A material that can efficiently transmit ultrasonic wave is enough for the elements.

The fuel level detecting apparatus 1 according to the above-described first to fourth embodiments of the present invention is provided with the step 41 in the guide pipe. However, the liquid level detecting apparatus according to the present invention may have a construction without the step 41. In this case, a temperature of the fuel 13 in the fuel tank 2 is detected by a temperature sensor (not shown) for example. Then, the transmission speed of the ultrasonic wave in the fuel 13 is corrected with the temperature, and the height H of the liquid level is calculated. In this manner, the height H of the liquid level 13a can be calculated with high accuracy.

In the first to fourth embodiments is described an example to adapt the liquid level detecting apparatus according to the present invention to the fuel level detecting apparatus 1 of an automobile. Alternatively, the liquid level detecting apparatus according to the present invention can be applied to other kinds of apparatus other than the fuel level detecting apparatus 1. For example, the liquid level detecting apparatus according to the present invention may be used for detecting liquid levels of other kinds of liquid mounted on the automobile such as engine oil, brake fluid or window washer liquid, or for detecting a liquid level in a liquid tank of a tank lorry. Further, the liquid level detecting apparatus according to the present invention may adapted for such purposes as to detect liquid levels in a liquid container in various kinds of equipment other than automobile and vehicle.

This description of the invention is merely exemplary in nature and, thus, variations that do not depart from the gist of the invention are intended to be within the scope of the invention. Such variations are not to be regarded as a departure from the spirit and scope of the invention.

What is claimed is:

1. A liquid level detecting apparatus for detecting a liquid level of a liquid in a liquid storage tank, comprising:
   an ultrasonic oscillation device that generates an ultrasonic wave and receives a reflection wave of the ultrasonic wave reflected on the liquid level;
   a reflector member that reflects the ultrasonic wave generated by the ultrasonic oscillation device to the liquid level and reflects the reflection wave to the ultrasonic oscillation device;
   a first path member that has a tubular shape and surrounds a first transmission path of the ultrasonic wave between the ultrasonic oscillation device and the reflector member;
   a second path member that has a tubular shape and surrounds a second transmission path of the ultrasonic wave between the reflector member and the liquid level;
   a holder that holds the reflector member, the first path member and the second path member at predetermined positions relative to one another; and
   a base member that is to be fixed on a bottom of the liquid storage tank and supports the holder rotatably about a rotational axis in parallel with the first path member to fold the holder from an upright position to place the second path member on the second transmission path to a folded position to position closer to the bottom of the liquid storage tank than the upright position.

2. The liquid level detecting apparatus according to claim 1, wherein the base member has a stopper means that stops a rotational movement of the holder about the first path member at the upright position.

3. The liquid level detecting apparatus according to claim 1, wherein the base member has an urging means that urges the holder from the folded position to the upright position.

4. The liquid level detecting apparatus according to claim 1, wherein the rotational axis approximately agrees with a longitudinal center axis of the first path member.

5. The liquid level detecting apparatus according to claim 4, wherein the base member has a torsion coil spring that is disposed approximately coaxially to the longitudinal center axis of the first path member to urge the holder from the folded position to the upright position.

6. The liquid level detecting apparatus according to claim 1, wherein the base member further supports a second apparatus thereon to secure a predetermined distance from the first path member and the second path member when the holder is at the upright position.

7. The liquid level detecting apparatus according to claim 5, wherein the second apparatus is a pump that feeds the liquid.

* * * * *